US008474451B2

(12) United States Patent
Cuzyldo et al.

(10) Patent No.: US 8,474,451 B2
(45) Date of Patent: Jul. 2, 2013

(54) DEVICE WITH OUTLET FOR CONTROLLING ANESTHETIC FLOW

(75) Inventors: Michael Cuzyldo, Orchard Park, NY (US); Michael Ide, Amherst, NY (US)

(73) Assignee: Piramal Critical Care, Inc., Orchard Park, NY (US)

( * ) Notice: Subject to any disclaimer, the term of this patent is extended or adjusted under 35 U.S.C. 154(b) by 722 days.

(21) Appl. No.: 12/608,092

(22) Filed: Oct. 29, 2009

(65) Prior Publication Data

US 2010/0199988 A1    Aug. 12, 2010

Related U.S. Application Data

(60) Provisional application No. 61/110,417, filed on Oct. 31, 2008.

(51) Int. Cl.
*A61M 11/00* (2006.01)

(52) U.S. Cl.
USPC .............. 128/203.14; 141/346; 141/351

(58) Field of Classification Search
USPC ............ 128/203.14, 200.14, 200.18, 200.19, 128/200.21, 203, 203.13; 141/364, 369, 346, 141/379–381, 351
See application file for complete search history.

(56) References Cited

U.S. PATENT DOCUMENTS

| 2,584,167 | A |   | 2/1952 | Sundholm |
| 2,597,775 | A |   | 5/1952 | Brown |
| 2,989,091 | A | * | 6/1961 | Lowenthal ................ 141/294 |
| 3,216,630 | A |   | 11/1965 | Stull |
| RE26,193 | E | * | 4/1967 | Labat ...................... 141/295 |
| 3,326,402 | A |   | 6/1967 | Randazzo |
| 3,720,352 | A |   | 3/1973 | Kozlowski |
| 3,744,526 | A |   | 7/1973 | MacNiel |
| 4,421,297 | A |   | 12/1983 | Pongrass et al. |
| 4,509,554 | A | * | 4/1985 | Failla .................... 137/614.05 |
| 4,949,875 | A |   | 8/1990 | Kuo |
| 5,026,924 | A |   | 6/1991 | Cicco |
| 5,287,898 | A |   | 2/1994 | Falb et al. |
| 5,381,836 | A |   | 1/1995 | Braatz et al. |
| 5,427,145 | A |   | 6/1995 | Grabenkort |
| 5,488,973 | A |   | 2/1996 | Yamamuro |
| 5,505,236 | A |   | 4/1996 | Grabenkort et al. |

(Continued)

FOREIGN PATENT DOCUMENTS

RU    2329832    7/2008
SU    1678380    9/1991

OTHER PUBLICATIONS

International Search Report corresponding to International Application No. PCT/US2009/051397 dated Sep. 15, 2009.

(Continued)

*Primary Examiner* — Steven Douglas
(74) *Attorney, Agent, or Firm* — Marc S. Kaufman; Reed Smith LLP (57) ABSTRACT

An apparatus and system for transferring a liquid, such as an anesthetic, from a reservoir to a machine while effectively minimizing the release of the liquid to the surrounding environment. The apparatus can include a first and a second component wherein twisting the first component and second component relative to each other causes a protrusion to seal or unseal a through-hole thereby allowing or preventing the flow of fluid and wherein a portion of an exterior surface of the second component that mates with a vaporizer has a polygonal shape with three or more flat sides.

20 Claims, 8 Drawing Sheets

U.S. PATENT DOCUMENTS

| | | | |
|---|---|---|---|
| 5,609,276 A * | 3/1997 | Greatbatch | 222/520 |
| 5,617,906 A | 4/1997 | Braatz et al. | |
| 5,682,874 A * | 11/1997 | Grabenkort et al. | 128/200.14 |
| 5,687,777 A | 11/1997 | Dobson et al. | |
| 5,915,427 A * | 6/1999 | Grabenkort | 141/364 |
| 6,135,329 A | 10/2000 | Stoneberg et al. | |
| 6,286,505 B1 | 9/2001 | Psaros | |
| 6,296,623 B2 | 10/2001 | Spinello | |
| 6,582,415 B1 | 6/2003 | Fowles et al. | |
| 6,585,016 B1 | 7/2003 | Falligant et al. | |
| 6,758,376 B1 | 7/2004 | Clodfelter et al. | |
| 6,800,786 B1 | 10/2004 | Rozov et al. | |
| 6,817,390 B2 | 11/2004 | Falligant et al. | |
| 7,159,616 B2 | 1/2007 | Watson et al. | |
| 7,546,856 B2 | 6/2009 | Chotenovsky | |
| 2006/0130930 A1 | 6/2006 | Turker et al. | |
| 2007/0066955 A1 | 3/2007 | Sparholt et al. | |
| 2007/0131725 A1 | 6/2007 | Friedman | |
| 2007/0199616 A1 | 8/2007 | Chotenovsky | |
| 2007/0204931 A1 | 9/2007 | Freed et al. | |
| 2007/0204932 A1 | 9/2007 | Freed et al. | |
| 2008/0302836 A1 * | 12/2008 | Mathis | 222/521 |
| 2009/0260627 A1 | 10/2009 | Cuzydlo et al. | |
| 2010/0018528 A1 | 1/2010 | Cuzydlo | |
| 2010/0018607 A1 | 1/2010 | Cuzydlo | |
| 2010/0108184 A1 | 5/2010 | Cuzydlo | |
| 2010/0199987 A1 | 8/2010 | Cuzydlo | |
| 2010/0199989 A1 | 8/2010 | Cuzydlo | |
| 2010/0199990 A1 | 8/2010 | Cuzydlo | |
| 2010/0224285 A1 | 9/2010 | Cuzydlo | |
| 2010/0319690 A1 | 12/2010 | Cuzydlo | |

OTHER PUBLICATIONS

International Search Report corresponding to International Application No. PCT/US2009/051391 dated Sep. 17, 2009.
International Search Report corresponding to International Application No. PCT/US2009/62465 dated Jan. 14, 2010.
International Search Report corresponding to International Application No. PCT/US2009/62461 dated Feb. 12, 2010.
International Search Report corresponding to International Application No. PCT/US2009/066535 dated Mar. 12, 2010.
International Search Report corresponding to International Application No. PCT/US2010/026317 dated May 19, 2010.
International Search Report corresponding to International Application No. PCT/US2010/038179 dated Aug. 11, 2010.
International Preliminary Report on Patentability corresponding to International Application No. PCT/US2009/051391 dated Feb. 3, 2011.
International Preliminary Report on Patentability corresponding to International Application No. PCT/US2009/051397 dated Feb. 3, 2011.
Search Report TR 10/066 established by Russian Patent Office corresponding to Turkish Application No. 2009/08207 dated Aug. 9, 2010.
Search Report TR 09/591 established by Russian Patent Office corresponding to Turkish Application No. 2009/07308 dated Jun. 10, 2010.
Search Report TR 10/041 established by Russian Patent Office corresponding to Turkish Application No. 2009/00676 dated Aug. 9, 2010.
Search Report TR 10/130 established by Russian Patent Office corresponding to Turkish Application No. 2009/09123 dated Sep. 14, 2010.
Examination Report TR 08/349 corresponding to Turkish Application No. 2007/03378 dated Jan. 19, 2009.
Examination Report TR 09/551 corresponding to Turkish Application No. 2007/03378 dated May 10, 2010.
Office Action Dated Jun. 22, 2012 in U.S. Appl. No. 12/496,895, Confirmation No. 5380.
Office Action Dated Mar. 7, 2012 in U.S. Appl. No. 12/274,819, Confirmation No. 1977.
Office Action Dated Sep. 26, 2011 in U.S. Appl. No. 12/274,819, Confirmation No. 1977.
International Search Report corresponding to International Application No. PCT/US09/62460.
Office Action Dated Apr. 27, 2012 in U.S. Appl. No. 12/608,081, Confirmation No. 5812.
Office Action Dated May 16, 2012 in U.S. Appl. No. 12/608,092, Confirmation No. 5825.
Office Action Dated May 23, 2012 in U.S. Appl. No. 12/630,174, Confirmation No. 9260.
Office Action Dated May 23, 2012 in U.S. Appl. No. 12/631,936, Confirmation No. 2889.
International Search Report corresponding to International Application No. PCT/US09/66920.

* cited by examiner

DEVICE WITH OUTLET FOR CONTROLLING ANESTHETIC FLOW

CROSS-REFERENCE TO RELATED APPLICATION

This application claims the benefit under 35 U.S.C. §119 (e) of the earlier filing date of U.S. Provisional Application Ser. No. 61/110,417 filed on Oct. 31, 2008, the entire disclosure of which is hereby incorporated by reference herein as if being set forth in its entirety.

FIELD OF INVENTION

This application discloses an invention which is related, generally and in various embodiments, to a device for supplying a liquid to a machine, such as a vaporizer.

BACKGROUND OF THE INVENTION

Liquid anesthetics are often packaged in glass bottles and shipped to a location where they may be used to anesthetize a patient, who is undergoing a medical or dental procedure. Such anesthetics may also be used to induce analgesia in a patient who is undergoing a medical or dental procedure. In order to administer the anesthetic, the contents of the glass bottle are placed in a vaporizer. The vaporizer may be used to vaporize the anesthetic, and provide the vaporized anesthetic in a desired amount to the patient.

Inhalable anesthetics are typically volatile substances with relatively low boiling points and high vapor pressure. Preferably, the anesthetic should be used in a way which will ensure there is little or no release to the atmosphere at all stages of handing. In order to transfer the liquid anesthetic to the vaporizer, the bottle must be opened. Since it is unwise to expose medical personnel performing the procedure to the anesthetic, and since anesthetics are expensive, devices have been developed to minimize the release of the anesthetic from the bottle to the environment surrounding the vaporizer to the environment surrounding a vaporizer. These devices, however, have failed to effectively minimize the release of anesthetic.

SUMMARY OF THE INVENTION

This application discloses an apparatus and system for transferring a liquid, such as an anesthetic, from a reservoir to a machine while effectively minimizing the release of the liquid to the surrounding environment. A apparatus can include a first component having a base and a nozzle, the base being configured so as to be capable of being sealed and affixed to an opening of a reservoir, the nozzle being externally threaded, and wherein a through-hole extends through the base and the nozzle, a second component having an aperture defined by an inner surface of the second component, wherein a portion of an exterior surface of the second component that mates with a vaporizer has a polygonal shape with three or more flat sides, and wherein the aperture has internal threads for engaging with the external threads of the nozzle, a support member extending into the aperture from the inner surface, a protrusion extending from the support member toward the internal threads, wherein the protrusion is configured to be capable of sealing the through-hole in the nozzle, wherein a fluid in the reservoir may exit the reservoir by way of the through-hole and the aperture; and wherein twisting the first component and second component relative to each other causes the protrusion to seal or unseal the through-hole thereby allowing or preventing the flow of fluid.

DETAILED DESCRIPTION OF THE INVENTION

The accompanying drawings are intended to provide further understanding of the invention and are incorporated in and constitute a part of the description of the invention. The drawings illustrate an embodiment of the invention and together with the description illustrate principles of the invention.

The drawings should not be taken as implying any necessary limitation on the essential scope of invention. The drawings are given by way of non-limitative example to explain the nature of the invention.

For a more complete understanding of the instant invention reference is now made to the following description taken in conjunction with accompanying drawings.

The various features of novelty which characterize the invention are pointed out specifically in the claims which are a part of this description. For a better understanding of the invention, reference should be made to the drawings and descriptive matter in which there are illustrated and described preferred embodiments of invention.

Figure 1:
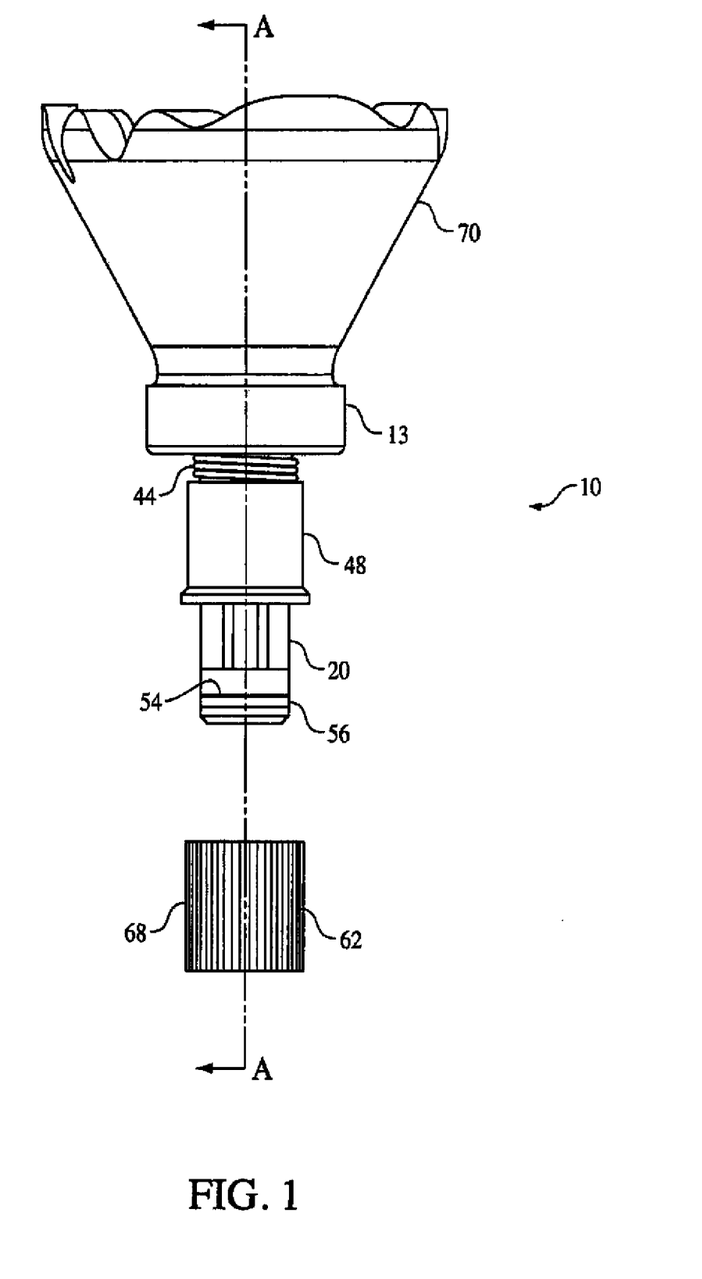
FIG. 1 illustrates a device according to an embodiment of the invention connected to an anesthetic.
Figure 2:
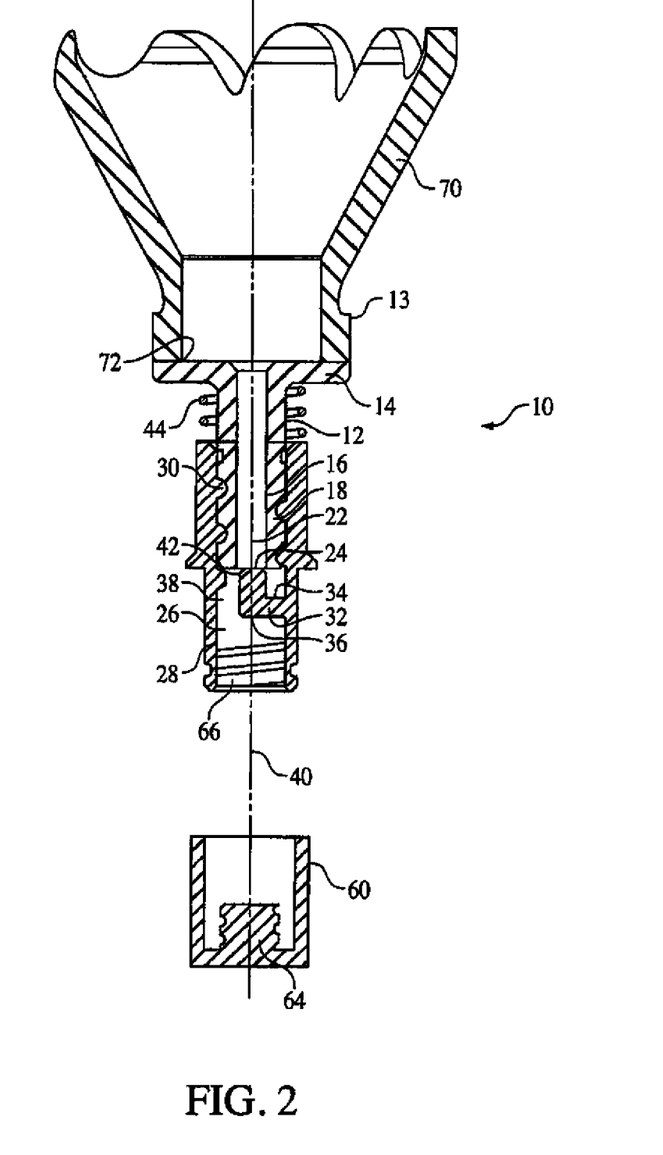
FIG. 2 illustrates a cross-section the device shown in FIG. 1 taken along A-A.
Figure 3A:
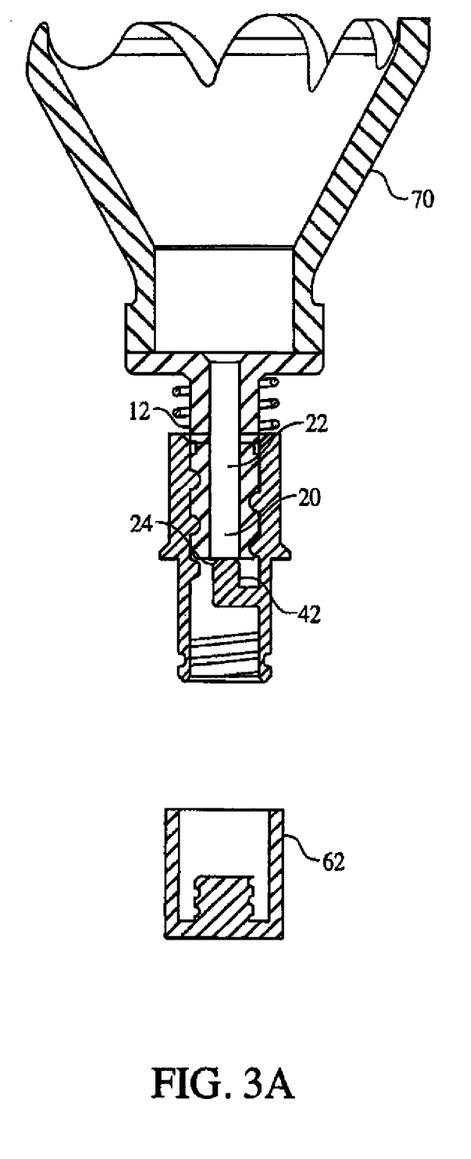
FIG. 3A illustrates a cross-section (along A-A) of the device shown in FIGS. 1 and 2 showing the device in an "open" position.
Figure 3B:
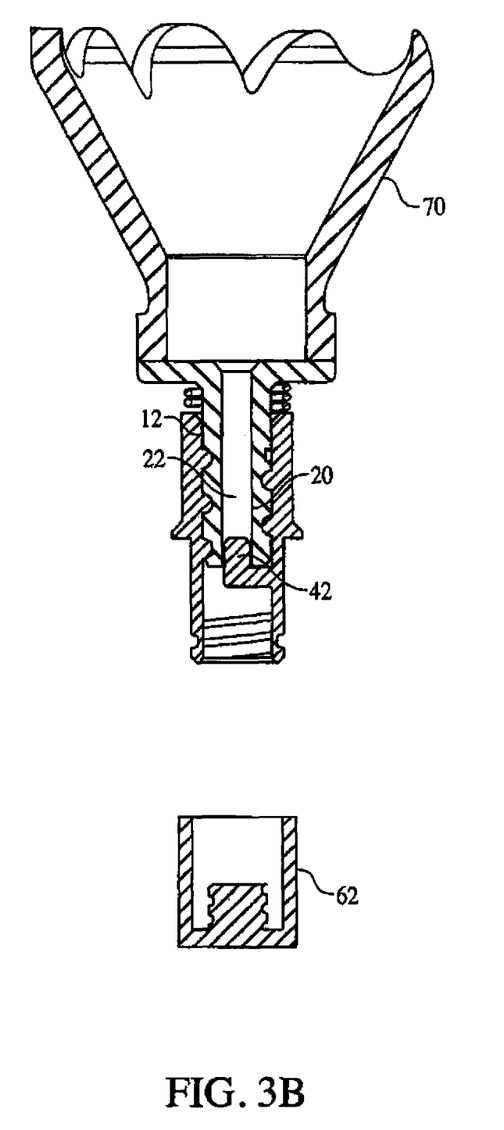
FIG. 3B illustrates a cross-section (along A-A) of the device shown in FIGS. 1 and 2 showing the device in the "closed" position.

Referring now to the drawings, wherein like numerals designate identical or corresponding parts throughout the referred views, FIG. 1 shows an embodiment of an apparatus 10 for selectively opening or closing an anesthetic reservoir 70. Such a device 10 may include a first component 12 adaptable to the reservoir 70 and a second component 20 adaptable to a vaporizer. The first component 12 may have a base 14 and a nozzle 16. The first component 12 may be attached to the reservoir 70 so that the base 14 may be in a sealing relation with an opening 72 of the reservoir 70. The base 14 may be attached to the reservoir using, for example, a clamping ring 13. The nozzle 16 may have an externally threaded portion 18. A through-hold 22 may extend through the base 14 and the nozzle 16. In this manner, a liquid contained within the reservoir 70 may flow fro the reservoir 70 through the through-hole 22 and exit an orifice 24 in the first component 12. For example, it may be desired to transfer anesthetic from the reservoir 70 to a machine, such as a vaporizer, which dispenses the anesthetic to a person undergoing a medical procedure.

Figure 4A:
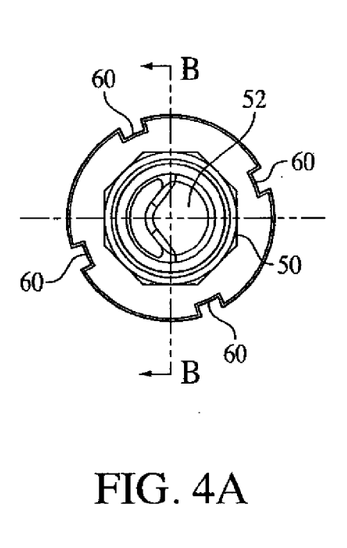
FIG. 4A illustrates an embodiment of the second component of a device according to an embodiment of the invention as viewed along the aperture.
Figure 4B:
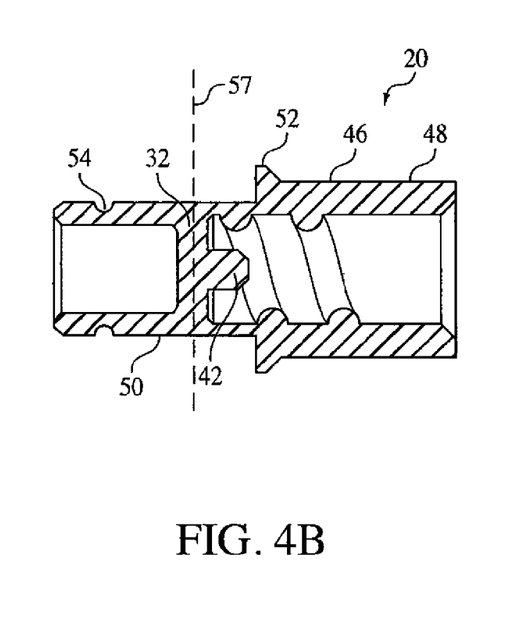
FIG. 4B is a cross-sectional view of the second component shown in FIG. 4A taken along B-B in FIG. 4A.
Figure 5A:
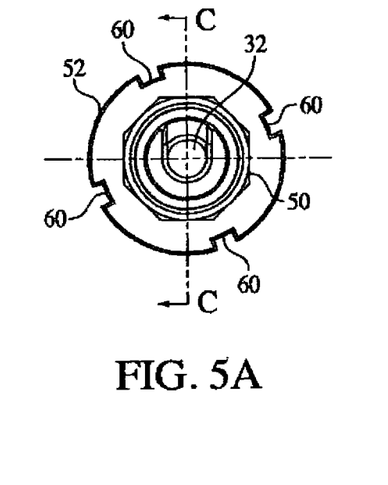
FIG. 5A illustrates another embodiment of the second component of a device according to the invention as viewed along the aperture.
Figure 5B:
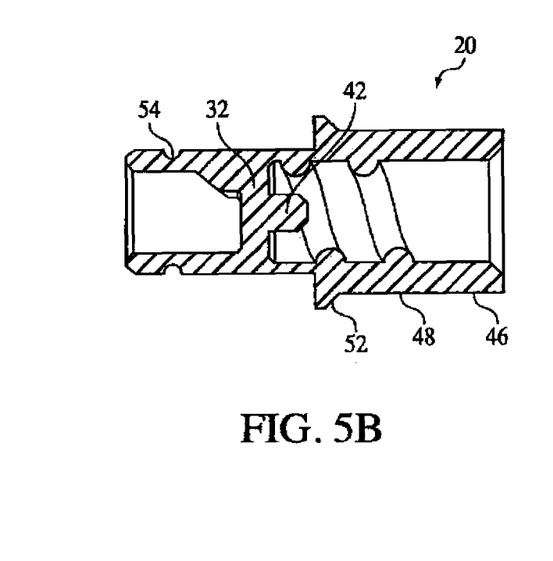
FIG. 5B is a cross-sectional view of the second component shown in FIG. 5A taken along C-C in FIG. 5A.

The second component 20 may have an aperture 26 defined by an inner surface 28. The inner surface 28 may have an internally threaded portion 30 to receive the externally threaded portion 18 of the nozzle 16. A support member 32 may extend into the aperture 26 from the inner surface 28. The support member 32 may occlude a portion of the aperture 26 but does not divide the aperture 26. In this manner, there may be a single passageway 38 leading from a first side 34 of the support member 32 to a second side 36 of the support member 32. The support member 32 may be oriented such that a primary plane 57 of the support member 32 is substantially transverse to the aperture 26 (see, e.g., FIGS. 4A and 4B). In an alternative embodiment, the support member 32 may be oriented such that a primary plane 59 of the support member 32 is substantially parallel to an axis 40 of the aperture 26 (see, e.g., FIGS. 5A and 5B).

A knob or protrusion 42 may extend from support member 32 toward the internally threaded portion 30. In this manner, by twisting the first component 12 and second component 20 relative to each other, the externally and internally threaded portions 18, 30 may cause the knob 42 to move toward or away from the orifice 24, depending on the direction in which twisting occurs. The knob 42 may be caused to be inserted in the orifice 24 and seated against the nozzle 16 thereby preventing liquid, which may be contained in the reservoir 70, from traveling from the reservoir 70 through the orifice 24 via the through-hole 22.

In operation, a single path is provided for liquid to travel from the reservoir 70, through the through-hole 22 of the first component 12, and through the aperture of the second component 20. Similarly, vapor may travel in the opposite direction to the reservoir 70 along the same path. Because only a single path is provided, liquid will not travel from the reservoir 70 along this path at the same time that vapor is traveling into the reservoir 70, and vice versa. Instead, only liquid or only vapor will be contained in the path at any given time, thereby creating a gurgling effect as the alternate movement of liquid out and then vapor in occurs.

A torsion spring 44 may be attached to the first component 12 and the second component 20 in order to provide a spring force to bias the first component 12 and the second component 20 to a pre-determined position relative to each other. The torsion spring 44 may bias the device 10 to a "closed" position wherein the knob 42 is seated in the orifice 24 and against the nozzle 16 as described above. In this manner, anesthetic in the reservoir 70 can not escape unless a force is applied to the second component 20 to counter the force imposed by the torsion spring 44.

The exterior surface 46 of the second component 20 may have a first portion 48 adapted for extending from a vaporizer, and a second portion 50 adapted for insertion into a vaporizer. The first portion 48 may be a smooth cylindrical shape in which a circumference of a cross-section transverse to axis 40 may have a rounded shape with no flat sides (see, e.g., FIGS. 5C and 5D). Alternatively, the first portion 48 may be a polygonal shape with three or more flat sides in combination with three or more rounded edges. The first portion 48 may be adapted for engaging a vaporizer.

Figure 4C:
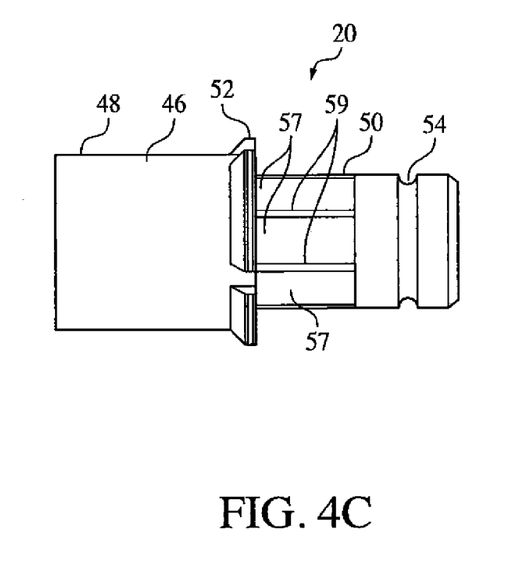
FIG. 4C is a side view of the second component shown in FIGS. 4A and 4B.
Figure 5C:
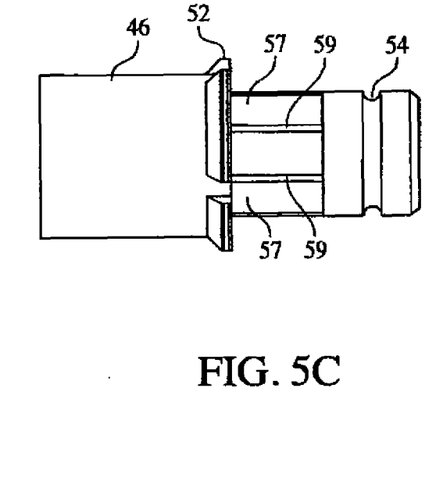
FIG. 5C is a side view of the second component shown in FIGS. 5A and 5B.
Figure 5D:
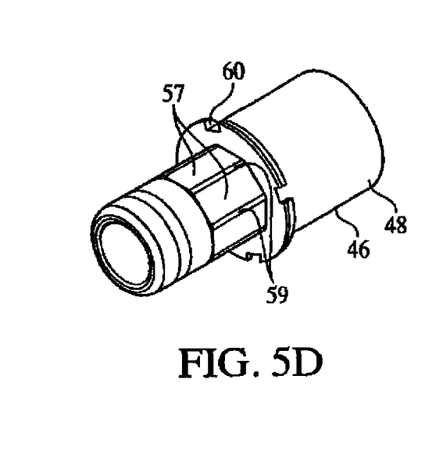
FIG. 5D is a perspective view of the second component shown in FIGS. 5A, 5B, and 5C.

A part of the second portion 50 may be a polygonal shape with three or more flat sides 57 in combination with three or more rounded edges 59 (see, e.g., FIGS. 4C, 5C, and 5D). The second portion 50 may have a groove 54 into which an O-ring 56 may be inserted to ensure a fluid-tight seal when connected to a vaporizer.

A transitional flange 52 may be provided to engage with a locking or holding device which may be located on a vaporizer. By engaging a vaporizer with the first portion 48, the transitional flange 52, or some combination of these, the device may be changed from a closed position to an open position while mounted to the vaporizer by rotating the reservoir 70.

Figure 6A:
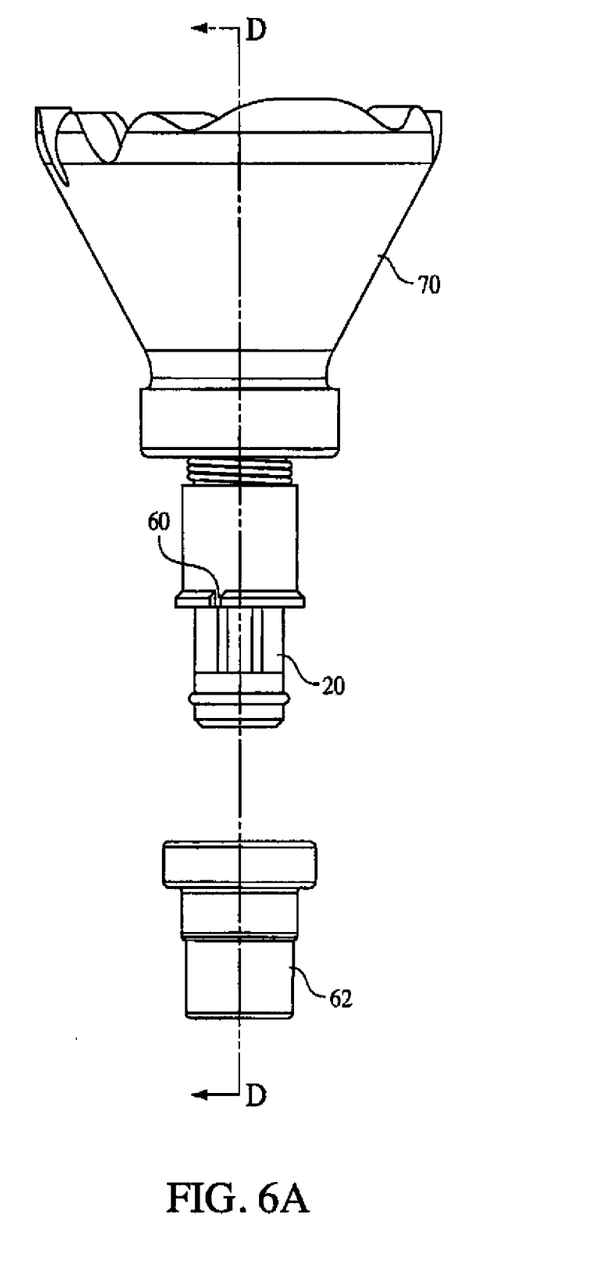
FIG. 6A is a side view of a device according to another embodiment of the invention.
Figure 6B:
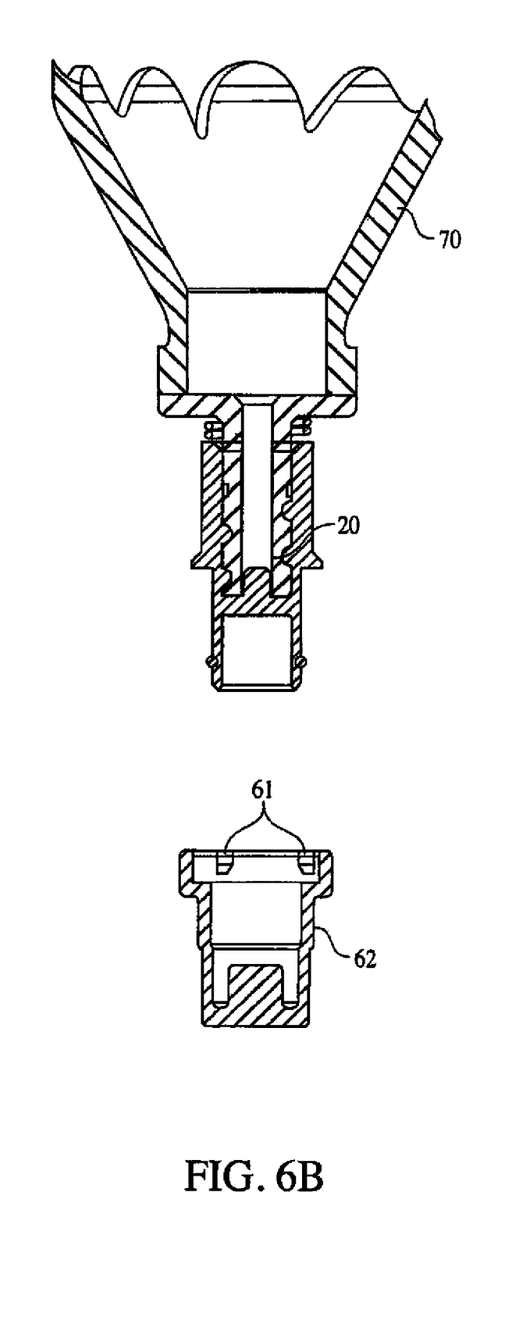
FIG. 6B is a cross-sectional view of the device shown in FIG. 6A taken along D-D.

A cap 62 may be provided for covering the device 10 when not in use in a vaporizer. The cap 62 may have an externally threaded plug 64 which may engage with an internally-threaded outlet 66 of the second component 20 to secure the cap 62 to the device 10. The exterior surface 68 of the cap 62 may be knurled for improved grip. In another embodiment, the cap 62 may have tabs for engaging notches 60 which may be in the transitional flange 52 (see, e.g., FIGS. 6A and 6B).

It is to be understood that the descriptions of the invention have been simplified to illustrate characteristics that are relevant for a clear understanding of the invention. Those of ordinary skill in the art may recognize that other elements or steps are desirable or required in implementing the invention. However, because such elements or steps are well known in the art, and because they do not facilitate a better understanding of the invention, a discussion of such elements or steps is not provided herein. The disclosure herein is directed to all such variations and modifications to such elements and methods known to those skilled in the art.

It is to be understood that the invention may assume various alternative orientations and step sequences, except where expressly specified to the contrary. It is also to be understood that the specific devices and processes illustrated in the attached drawings, and described in this specification are simply exemplary embodiments of the inventive concepts defined in the appended claims. Hence, specific dimensions and other physical characteristics relating to the embodiments disclosed herein are not to be considered as limiting, unless the claims expressly state otherwise.

Further, since numerous modifications and changes will readily occur to those skilled in the art, it is not desired to limit the invention to the exact construction and operation shown and described, and accordingly all suitable modifications and equivalents may be regarded as falling within the scope of the invention as defined by the claims that follow.

What is claimed is:

1. An apparatus for controlling the flow of anesthetic from an anesthetic reservoir comprising:
   a first component having a base and a nozzle, the base being configured to be sealed and to be affixed to an opening of a reservoir, the nozzle being externally threaded, and wherein a through-hole extends through the base and the nozzle;
   a second component having an aperture defined by an inner surface of the second component, and wherein the aperture has internal threads for engaging with the external threads of the nozzle;
   a support member extending into the aperture from the inner surface;
   a protrusion extending from the support member toward the internal threads, wherein the protrusion is configured to seal the through-hole in the nozzle;

a biasing member attached to the first component and the second component and the biasing member biasing the second component relative to the first component to cause the protrusion to seal the through-hole;

wherein a fluid in the reservoir may exit the reservoir by way of the through-hole and the aperture; and wherein twisting the first component and second component relative to each other causes the protrusion to seal or unseal the through-hole thereby allowing or preventing the flow of fluid.

2. The apparatus of claim 1, wherein the biasing member is a torsion spring.

3. The apparatus of claim 1, wherein a primary plane of the support member is substantially transverse with respect to the aperture.

4. The apparatus of claim 1, wherein a primary plane of the support member is substantially parallel to an axis of the aperture.

5. The apparatus of claim 1, further comprising a cap.

6. The apparatus of claim 1, further comprising an O-ring affixed to the exterior surface of the second component.

7. The apparatus of claim 1, wherein the exterior surface of the second component is adapted for engaging a vaporizer to prevent the second component from rotating relative to the vaporizer.

8. The apparatus of claim 1, wherein a portion of an exterior surface of the second component that mates with a vaporizer has a polygonal shape with three or more flat sides.

9. A system comprising:

an anesthetic reservoir; and an apparatus for controlling the flow of anesthetic from the anesthetic reservoir comprising:

a first component having a base and a nozzle, the base being configured to be sealed and to be affixed to an opening of a reservoir, the nozzle being externally threaded, and wherein a through-hole extends through the base and the nozzle;

a second component having an aperture defined by an inner surface of the second component, and wherein the aperture has internal threads for engaging with the external threads of the nozzle;

a support member extending into the aperture from the inner surface;

a protrusion extending from the support member toward the internal threads, wherein the protrusion is configured to seal the through-hole in the nozzle;

a biasing member attached to the first component and the second component and the biasing member biasing the second component relative to the first component to cause the protrusion to seal the through-hole;

wherein a fluid in the reservoir may exit the reservoir by way of the through-hole and the aperture; and wherein twisting the first component and second component relative to each other causes the protrusion to seal or unseal the through-hole thereby allowing or preventing the flow of fluid.

10. The system of claim 9, wherein the biasing member is a torsion spring.

11. The system of claim 9, wherein a primary plane of the support member is substantially transverse with respect to the aperture.

12. The system of claim 9, wherein a primary plane of the support member is substantially parallel to an axis of the aperture.

13. The system of claim 9, further comprising a cap.

14. The system of claim 9, further comprising an O-ring affixed to the exterior surface of the second component.

15. The system of claim 9, wherein the exterior surface of the second component is adapted for engaging a vaporizer to prevent the second component from rotating relative to the vaporizer.

16. The system of claim 9, wherein a portion of an exterior surface of the second component that mates with a vaporizer has a polygonal shape with three or more flat sides.

17. The system of claim 9, further comprising a machine connected to the apparatus.

18. The system of claim 17, wherein the machine is a vaporizer.

19. The apparatus of claim 1, wherein the base of the first component is affixed to the opening of the reservoir with a clamping ring.

20. The system of claim 9, wherein the base of the first component is affixed to the opening of the reservoir with a clamping ring.

* * * * *

UNITED STATES PATENT AND TRADEMARK OFFICE
CERTIFICATE OF CORRECTION

PATENT NO. : 8,474,451 B2  
APPLICATION NO. : 12/608092  
DATED : July 2, 2013  
INVENTOR(S) : Cuzydlo et al.

Page 1 of 1

It is certified that error appears in the above-identified patent and that said Letters Patent is hereby corrected as shown below:

On the title page, items 12 and 75:

First inventor's last name on the patent reads: Cuzyldo et al.

First inventor's last name on the patent should read: Cuzydlo et al.

Signed and Sealed this
Twenty-fourth Day of December, 2013

Margaret A. Focarino
*Commissioner for Patents of the United States Patent and Trademark Office*